United States Patent [19]

Newman et al.

[11] Patent Number: 5,009,637

[45] Date of Patent: Apr. 23, 1991

[54] APPARATUS FOR HYPODERMIC INJECTION OF LIQUIDS

[75] Inventors: Jack Newman, Queenscliff; James A. Monroe, Turramurra, both of Australia

[73] Assignee: Sy-Quest International Limited, Woolahra, Australia

[21] Appl. No.: 272,121

[22] Filed: Nov. 16, 1988

[30] Foreign Application Priority Data

Nov. 16, 1987 [AU] Australia ............................... PI5441

[51] Int. Cl.⁵ ................................................ A61M 5/30
[52] U.S. Cl. ............................................ 604/68; 604/70; 604/143; 604/208; 604/232
[58] Field of Search ............... 604/70, 68, 72, 140, 604/141, 143, 147–150, 208, 211, 232

[56] References Cited

U.S. PATENT DOCUMENTS

| | | | |
|---|---|---|---|
| 2,547,099 | 4/1951 | Smoot | 604/70 |
| 2,550,053 | 4/1951 | Ferguson | 604/70 |
| 2,645,223 | 7/1953 | Lawshe et al. | 604/70 |
| 2,764,977 | 10/1956 | Ferguson | 604/70 |
| 3,115,133 | 12/1963 | Morando | 604/70 |
| 3,292,621 | 12/1966 | Banker | 604/70 |
| 3,406,684 | 10/1968 | Tsujino | 604/70 |
| 3,815,785 | 6/1974 | Gilmont | 222/46 |
| 3,853,125 | 12/1974 | Clark et al. | 604/70 |
| 4,623,332 | 11/1986 | Lindmayer et al. | 604/68 |
| 4,790,824 | 12/1988 | Morrow et al. | 604/143 |
| 4,874,367 | 10/1989 | Edwards | 604/72 |
| 4,913,699 | 4/1990 | Parsons | 604/68 |
| 4,936,833 | 6/1990 | Sani | 604/232 |
| 4,941,880 | 7/1990 | Burns | 604/143 |

Primary Examiner—C. Fred Rosenbaum
Assistant Examiner—Mark O. Polutta
Attorney, Agent, or Firm—Ladas & Parry

[57] ABSTRACT

A device to introduce a liquid into the hypoderma, the device includes a reservoir which receives a gas under pressure, the gas is delivered via a valve to an interacting piston and cylinder. When the gas is delivered to the piston, the piston moves to eject a liquid from a capsule mounted within the device. The liquid contained in the capsule is then ejected through a nozzle located against the skin of the user.

9 Claims, 1 Drawing Sheet

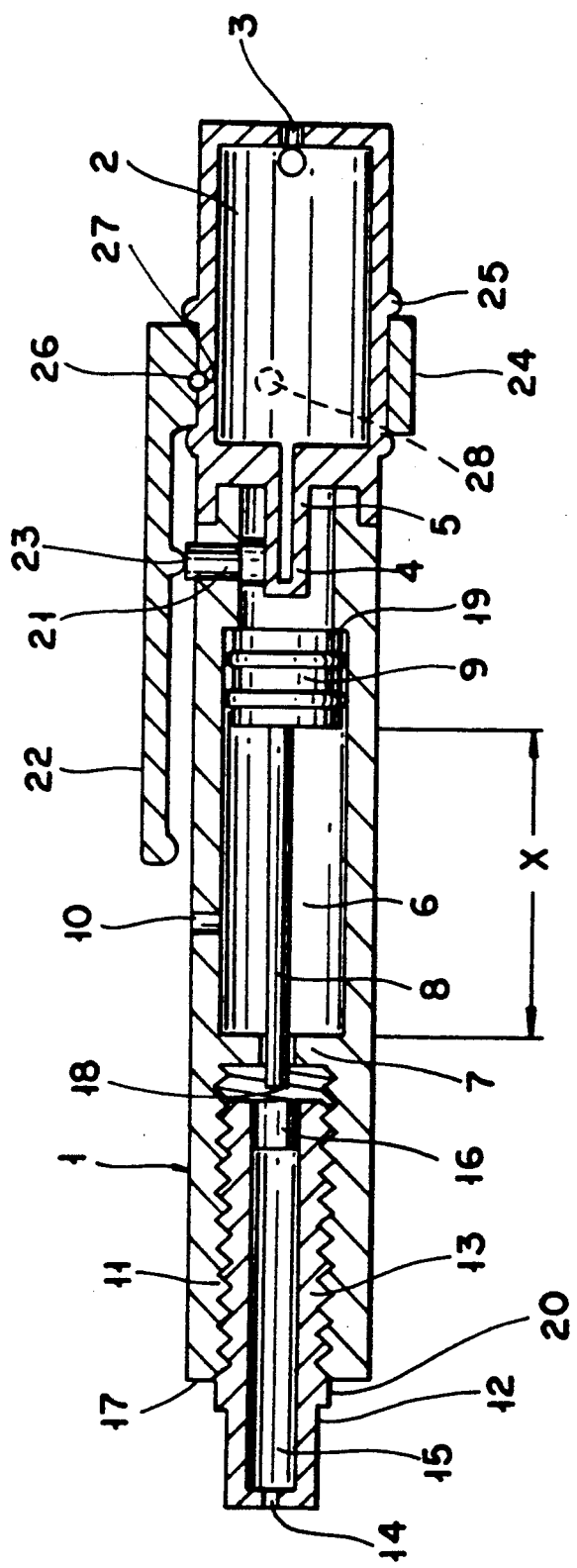

APPARATUS FOR HYPODERMIC INJECTION OF LIQUIDS

This invention relates to gas operated apparatus to introduce liquid into the hypoderma. Such devices have use in the administration of, for example, local anaesthetic and insulin and the like.

For many years it was the practice to deposit medicaments into the hypoderma by the use of a device including a tubular needle connected to a reservoir of medicament incorporating a piston. The needle was inserted through the epidermis into the hypoderma and the medicament was discharged by moving the piston along the reservoir. Such devices had several problems. Firstly, the penetration of the needle was a possible cause for infection and there was the patient resistance to the discomfort associated with the insertion of the needle.

Gas operated devices were devised as an alternative to needle devices. In the gas operated device liquid medicament was discharged from a reservoir through a port as a spray by a piston moved along the reservoir by subjecting it to a force created by the sudden release of gas. This device has the obvious advantage that there was no skin penetration and hence no discomfort and no possibility of infection.

The common forms of gas device comprised a holder to which was coupled to a container of medicament in a manner aligning it with the piston to be gas operated and which provided means to hold a gas filled capsule in the holder. By puncturing the capsule the gas was released into a cylinder and the piston therein was driven into the container to discharge the medicament through a port in the container.

Such an arrangement has several disadvantages. For example, the holder as provided was a large member and was complex having to provide securement means for the medicament container and the gas capsule. It had to provide a piston mounting arrangement and means to releasably hold the gas capsule securely in a gas tight manner and puncture the gas capsule. In short, the device was large and complex and correspondingly expensive.

Diclosed in PCT U.S. Application No. 86/02718 is a device within which a conventional syringe is mounted. Prior to mounting, the needle is removed and the device employs gas under pressure to cause the piston in the device to move to spray from the syringe body a stream of medication directed at the skin of the patient. This particular device has the disadvantage that it is generally complex to use and therefore time consuming. Firstly, the syringe is provided with a needle and a liquid medication drawn into the syringe. The needle is then removed and the syringe mounted within the device. The device is then applied to the skin and operated.

It is the object of the present invention to overcome or substantially ameliorate the above disadvantages.

There is disclosed herein a device to introduce a liquid into a patient, said liquid being contained in a capsule which includes a hollow body with a nozzle end through which the liquid exits from within the capsule, and a capsule piston movably mounted within the body and operable to push the liquid out through said nozzle end, said device comprising:

a body providing a reservior to receive a gas under pressure;

an interacting actuator piston and cylinder providing a variable volume space, with said cylinder being fixed to said body;

duct means extending from said reservoir to said space;

operator manipulable valve means closing said duct and operable by a user to open said duct to permit gas to pass from said reservoir to said space to cause movement of said actuator piston within said cylinder;

a capsule mounting to receive a capsule; and a piston rod extending from said actuator piston and extending therefrom towards said mounting and engageable with the capsule piston to cause movement thereof upon gas under pressure being delivered to said space.

The present invention in its preferred form has been devised to overcome the above problems by providing a simple unitary apparatus which is provided complete with medicament and pressurised gas supply. A single use renders it unsuitable for further use and it must be thrown away. The design and the material of manufacture of the device proposed by the present invention makes it economically practical to throw the device away after a single usage.

To cater for the varying amounts of a medicament a user may require the present device in its preferred form to be adjustable so that a predetermined amount of the medicament can be discharged. This will mean that for some users there will be an amount of medicament thrown away at each treatment. As will be understood the cost of a medicament, such as insulin for a diabetic person, is quite small compared to the convenience of having a dosage adjustable inexpensive device that is convenient to carry and store, is economical to purchase and allows the administration of the insulin in a quick, simple and convenient manner. For the above reason it is proposed to provide a reservoir for the medicament which will cater for a range of dosages most likely to be needed and thereby allow the user to select the amount that is required to be administered A presently preferred embodiment of the invention will now be described with reference to the accompanying drawing. It is presently intended that the device will be made substantially completely from clear polycarbonate in an injection molding process.

As illustrated, the device comprises a body 1 with a gas reservoir 2 at one end having a valve 3 of known type whereby gas can be introduced into the reservoir 2 of a finished product. At the fore end of the reservoir there is a tubular neck 4 with a weak zone indicated 5 where the neck joins the reservoir. As will be understood if the neck is broken off the reservoir, the gas therein will escape. The selected material of manufacture allows the neck to be readily broken off.

The neck 4 extends into a tubular bore 6 in the body 1 which includes an annular shoulder 7. The shoulder 7 serves as a piston travel stop, as will be described, and a guide for a piston rod 8 having a piston head 9 sealingly slidably mounted in the bore 6. There is a gas escape vent 10 in the wall of the body 1 in communcation with the bore 6. The fore end of the bore 6 is threaded at 11.

A liquid medicament capsule 12 is provided as a fitment for the device. The capsule is externally threaded at 13 enabling it to be screwed into the bore threads 11. The capsule has a port 14 at its fore end and the port 14 is sealed by a seal that will yield when pressure is applied to liquid medicament housed in the bore 15 of the capsule 12. Pressure is applied to the medicament by a piston 16 slidably housed in the bore 15.

The exterior of the capsule 12 is marked in any suitable manner to indicate fractions of the capacity of the bore 15. For example there may be external markings on the capsule to divide the bore length into five sections each of Y mls. By threading the capsule 12 into the body the markings on the capsule will pass by a datum mark on the body, for example the end face 17 of the body 1 could be such a mark. Detent means is preferably provided whereby the detent is releasably engaged each time a graduation on the capsule 12 is aligned with the datum mark. In this way the capsule can be releasably locked in a desired position.

By axially moving the capsule 12 (as a result of rotating it) the position of the capsule 12 relative to the end 18 of the piston rod changes. When the capsule is fully "in" the maximum amount of medicament will be dispensed. By threading the capsule 12 "out" the amount of medicament dispensed can be reduced.

It will be noted that as illustrated the piston 9 is in its zero position against the shoulder 19. The stroke of the piston 9 is limited to the distance X and therefore when the capsule is threaded fully into the body so the shoulder 20 engages the end of the body the piston 16 will be adjacent the end 18 of the piston rod. The maximum stroke of the piston 16 is slightly greater than X. It follows that when the piston 9 moves the distance X, the piston 16 will move the same distance and substantially the whole of the medicament in the capsule 12 will be ejected. If the capsule is moved "out" of the body 1 the piston rod 18 will be spaced from the piston 16 and although the piston 9 will move X, the piston 16 will move less than X.

In order to release the gas in the capsule 2 there is a neck breaker in the form of a plunger 21. Pressure is applied to the plunger 21 by a flexible arm 22 through a lug 22 thereon. The arm 22 has a ring end 24 rotatably mounted on the body part 2 between shoulders 25. There is a detent 26 on the ring 24 shown engaged in a depression 27 in the body part 2 to align the lug 23 with the plunger 21. In the inoperative position the ring 24 would be rotated until the detent 26 engages in the recess 28 in the body part 2.

In an operational sequence, a capsule 12 would be fitted to the device and the amount of medicament to be dispensed would be chosen by the degree to which the capsule 12 is threaded into the body 1. The lug 23 would be placed over the plunger 21. The device would be positioned with the port 14 over the part of the user where the "injection" is to take place. The arm 22 would be depressed and the plunger 21 would be depressed and the neck 4 would be broken off the capsule 2. The gas would escape and drive the piston 9 the distance X until it engages the shoulder 7, at this time the port 10 would be uncovered and the gas behind the piston 9 would escape to atmosphere. Whilst the piston 9 is advancing the end 18 of the piston rod 8 would be driving the piston 16 in the capsule bore 15 causing the medicament therein to eject from the port 14. Depending upon the amount the capsule 12 is threaded into the body 1, the piston 16 will move the distance X or a fraction of that distance and the amount of medicament ejected will vary accordingly.

Whilst a presently preferred embodiment of the invention has been described hereinbefore it is to be understood that variations can be made to the specific embodiment described without departing from the inventive concept. By way of example only, the manner in which the piston 9 is regulated in its travel can be other than as disclosed. The manner in which the neck 4 is caused to be broken can be other than as described. The arm 22 may not be connected to the rotatable band 24 and may be a fixture on the body and merely be flexible up and down.

What we claim is:

1. A device for introducing a liquid into a patient, including: a capsule for containing the liquid, the capsule including a hollow body with a nozzle end through which the liquid exits from within the capsule, and a capsule piston movably mounted within the body and operable to push the liquid out through said nozzle end;
   - a body providing a reservoir for receiving a quantity of gas under pressure from a gas source;
   - an interacting actuator piston and cylinder assembly, within the body, providing a variable volume space behind the actuator piston;
   - a neck, having a closed end, extending from said reservoir to said space behind the actuator piston;
   - means operable by a user to open said closed end to permit said quantity of gas to pass from said reservoir to said space behind the actuator piston to cause movement of said actuator piston within said cylinder;
   - a piston rod extending from said actuator piston towards an anterior end of the body and engageable with the said capsule piston to cause movement thereof upon said quantity of gas under pressure being delivered to said space behind the actuator piston;
   - a casule mounting means, at the anterior end of the body, to connect the capsule to the body while allowing the capsule to be axially moveable along the anterior end so that the distance between the capsule piston and a front end of the piston rod can be varied so that the amount of penetration of the piston rod into the capsule, upon movement of the actuator piston, may be adjusted to vary the amount of liquid expelled from the capsule.

2. The device of claim 1 wherein said mounting means includes a threaded recess at the anterior end of the body, and external threads on the capsule that are received within said recess, so that rotation of the capsule axially moves the capsule along the anterior end of the body to adjust the position of the capsule.

3. The device of claim 2 wherein the mounting means further comprises detent means for engaging the capsule.

4. A device for introducing a liquid into a patient, including:
   - a capsule for containing the liquid, the capsule includes a hollow body with a nozzle end through which the liquid exits from the capsule, and a capsule piston movably mounted within the body and operable to push the liquid out through said nozzle end;
   - a body providing a reservoir for receiving a quantity of gas under pressure;
   - an interacting actuator piston and cylinder assembly, within the body, providing a variable volume space behind the actuator piston;
   - a frangible neck extending from said reservoir into said space behind the actuator piston;
   - means operable by a user to break said frangible neck to permit said gas to pass from said reservoir to said space behind the actuator piston to cause movement of said actuator piston within said cylinder;

a piston rod extending from said actuator piston towards an anterior end of the body and engageable with the said capsule piston to cause movement thereof upon said quantity of gas under pressure being delivered to said space behind the actuator piston; and a capsule mounting means, at the anterior end of the body, to connect the capsule to the body while allowing the capsule to be axially moveable along the anterior end so that the distance between the capsule piston and a front end of the piston rod can be varied so that the amount of penetration of the piston rod into the capsule, upon movement of the actuator piston, may be adjusted to vary the amount of liquid expelled from the capsule.

5. The device of claim 4 wherein said neck includes a weakened section, said neck being fracturable and wherein said device further includes trigger means operable by a user to fracture said neck.

6. The device of claim 4 wherein said cylinder and mounting means are integrally formed, said mounting means is internally threaded at the anterior end of the body, and wherein external threads on the capsule are received within said recess so that rotation of the capsule axially moves the capsule along the anterior end of the body to adjust the position of the capsule.

7. The device of claim 6 wherein said mounting means includes detent means for engaging the capsule.

8. The device of claim 4 wherein the means operable by a user to break said frangible neck further comprises a plunger which extends radially through the body adjacent the frangible neck.

9. The device of claim 8 further comprising a ring rotatably mounted on the body, the ring supporting an arm which is positionable over the plunder for facilitating activation of the plunger.

* * * * *